(12) United States Patent
Bai et al.

(10) Patent No.: US 10,144,637 B2
(45) Date of Patent: Dec. 4, 2018

(54) SENSOR BASED TRACKING TOOL FOR MEDICAL COMPONENTS

(71) Applicants: Yanhui Bai, Toronto (CA); Cameron Piron, Toronto (CA); Michael Wood, Toronto (CA); Thanh Vuong, Toronto (CA); Kelly Dyer, Toronto (CA); Gal Sela, Toronto (CA); Alex Panther, Toronto (CA)

(72) Inventors: Yanhui Bai, Toronto (CA); Cameron Piron, Toronto (CA); Michael Wood, Toronto (CA); Thanh Vuong, Toronto (CA); Kelly Dyer, Toronto (CA); Gal Sela, Toronto (CA); Alex Panther, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/525,478

(22) PCT Filed: Nov. 25, 2014

(86) PCT No.: PCT/CA2014/051122
§ 371 (c)(1),
(2) Date: May 9, 2017

(87) PCT Pub. No.: WO2016/082018
PCT Pub. Date: Jun. 2, 2016

(65) Prior Publication Data
US 2017/0327371 A1    Nov. 16, 2017

(51) Int. Cl.
*A61B 34/20*    (2016.01)
*B81B 7/02*    (2006.01)
(Continued)

(52) U.S. Cl.
CPC ............ *B81B 7/02* (2013.01); *A61B 34/20* (2016.02); *H04W 4/029* (2018.02); *H04W 4/38* (2018.02);
(Continued)

(58) Field of Classification Search
CPC . A61B 34/20; A61B 90/11; A61B 2017/3407; A61B 2090/3983;
(Continued)

(56) References Cited

U.S. PATENT DOCUMENTS 6,546,277 B1 *    4/2003    Franck .................. A61B 90/10
                                                          600/426
2001/0034530 A1 * 10/2001    Malackowski ........ A61B 90/36
                                                          606/130

(Continued)

FOREIGN PATENT DOCUMENTS

WO        2013091112 A1    6/2013

*Primary Examiner* — Elmer Chao
(74) *Attorney, Agent, or Firm* — Ridout & Maybee LLP

(57) ABSTRACT

A medical navigation system is provided. The medical navigation system includes a computing device having a processor coupled to a memory, a wireless communication component and a display for displaying an image. The medical navigation system further includes a sensor module attached to a medical device. The sensor module includes a housing for housing components of the sensor module and for attaching to the medical device, a processor housed in the housing, a memory coupled to the processor, a wireless communication component coupled to the processor, a battery coupled to the processor, and a sensor coupled to the processor. The sensor generates a signal to be transmitted wirelessly via the sensor module wireless communication component and receivable by the computing device wireless communication component, the signal representing movement of the medical device.

13 Claims, 11 Drawing Sheets

(51) Int. Cl.
*H04W 4/029* (2018.01)
*H04W 4/38* (2018.01)
*A61B 17/34* (2006.01)
*A61B 34/10* (2016.01)
*A61B 90/10* (2016.01)
*A61B 90/00* (2016.01)
*A61B 90/11* (2016.01)
*A61B 34/00* (2016.01)
*A61B 8/00* (2006.01)

(52) U.S. Cl.
CPC ............... *A61B 8/56* (2013.01); *A61B 90/11* (2016.02); *A61B 2017/3407* (2013.01); *A61B 2034/105* (2016.02); *A61B 2034/107* (2016.02); *A61B 2034/2051* (2016.02); *A61B 2034/2055* (2016.02); *A61B 2034/2068* (2016.02); *A61B 2034/256* (2016.02); *A61B 2090/101* (2016.02); *A61B 2090/376* (2016.02); *A61B 2090/3983* (2016.02)

(58) Field of Classification Search
CPC .... A61B 2034/2055; A61B 2034/2068; A61B 2034/105; A61B 2034/107; A61B 2034/2051; A61B 2034/256; A61B 2090/376; A61B 2090/101; B81B 7/02; H04W 4/029; H04W 4/38
See application file for complete search history.

(56) References Cited

U.S. PATENT DOCUMENTS

| | | |
|---|---|---|
| 2007/0016008 A1 | 1/2007 | Schoenefeld |
| 2007/0225550 A1 | 9/2007 | Gattani et al. |
| 2008/0030345 A1 | 2/2008 | Austin et al. |
| 2009/0055024 A1* | 2/2009 | Kay ............... B25J 9/1697 700/259 |
| 2011/0160583 A1* | 6/2011 | Roche ............... A61B 8/565 600/438 |
| 2014/0088410 A1 | 3/2014 | Wu |
| 2014/0135773 A1* | 5/2014 | Stein ............... G06F 19/3406 606/80 |
| 2014/0178832 A1 | 6/2014 | Choi et al. |

* cited by examiner

SENSOR BASED TRACKING TOOL FOR MEDICAL COMPONENTS

TECHNICAL FIELD

The present disclosure is generally related to image guided medical procedures, and more specifically to a sensor based tracking tool for medical components.

BACKGROUND

The present disclosure is generally related to image guided medical procedures using a surgical instrument, such as a fiber optic scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial reference of the patient as understood by the surgical system is as accurate as possible.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain. Surgical instruments would then be inserted down the access port 12.

Optical tracking systems, used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked.

Conventional systems have infrared (IR) cameras that track reflective markers such as spheres placed on a frame on a pointer, port, or positioning device arm. This system occupies considerable space and is tedious to set up. If the reflective markers are blocked by any object, the IR camera cannot detect the tool position accurately. Moreover, the IR cameras cannot offer surgical tool dynamic parameters such as tool moving speed, acceleration, rotation angle, etc., in order to monitor the surgical procedure. Therefore, there is a need for an improved approach for tracking medical components using a tracking system.

SUMMARY

One aspect of the present disclosure provides a medical navigation system. The medical navigation system includes a computing device having a processor coupled to a memory, a wireless communication component and a display for displaying an image. The medical navigation system further includes a sensor module attached to a medical device. The sensor module includes a housing for housing components of the sensor module and for attaching to the medical device, a processor housed in the housing, a memory coupled to the processor, a wireless communication component coupled to the processor, a battery coupled to the processor, and a sensor coupled to the processor. The sensor generates a signal to be transmitted wirelessly via the sensor module wireless communication component and receivable by the computing device wireless communication component, the signal representing movement of the medical device. The sensor module may include at least one of an accelerometer and a gyroscope.

Another aspect of the present disclosure provides a sensor module for attachment to a medical device and for use with a medical navigation system. The sensor module comprises a housing for housing components of the sensor module and for attaching to the medical device, a processor housed in the housing, a memory coupled to the processor, a communication component coupled to the processor, a battery coupled to the processor, and a sensor coupled to the processor. The sensor may include at least one of an accelerometer and a gyroscope. The housing may be in the form of a low profile sticker to be applied to the medical device or a collar to be applied to the medical device.

Another aspect of the present disclosure provides a method of establishing and monitoring a position of a medical device. The method is for use on a computing device of a medical navigation system. The computing device has a processor coupled to a memory, a wireless communication component and a display for displaying an image. The method comprises establishing an initial position of the medical device in space and receiving via the wireless communication component a signal representing movement of the medical device, the signal including information provided by an accelerometer and a gyroscope housed in a sensor module attached to the medical device. The processor may be further coupled to a camera and establishing an initial position of the medical device in space may include detecting a location in space of tracking markers temporarily placed on the medical device using an image signal provided to the processor by the camera. The method may further include displaying the initial position of the medical device on the display when the initial position is established and updating the position of the medical device on the display when the signal representing movement of the medical device is received.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
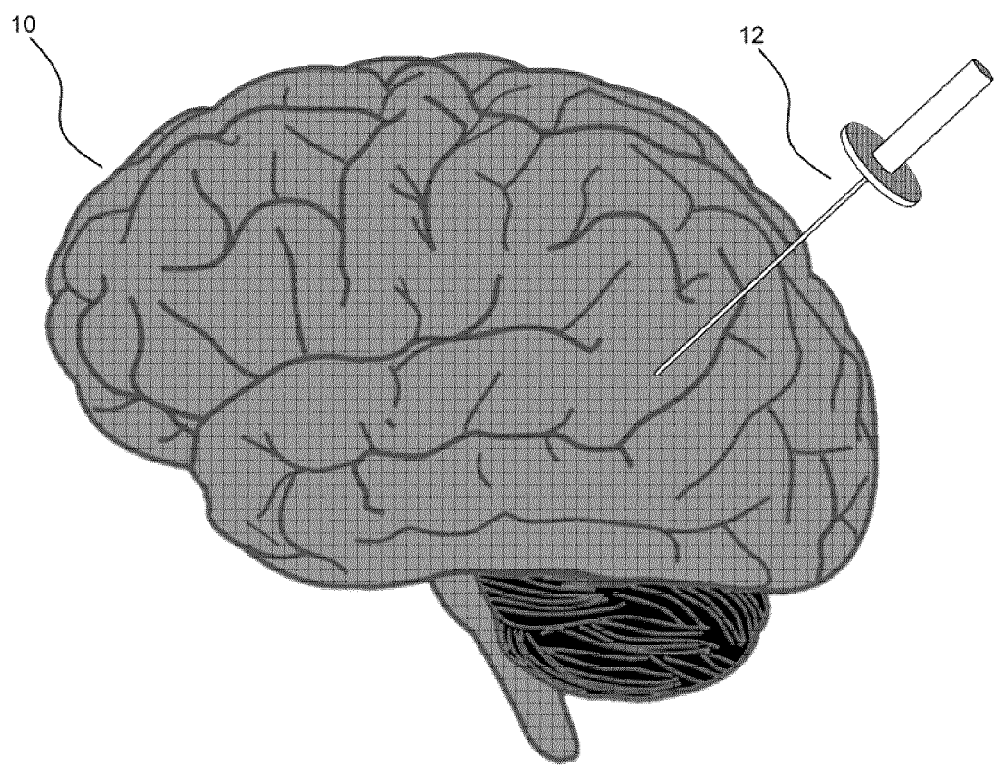
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Figure 2:
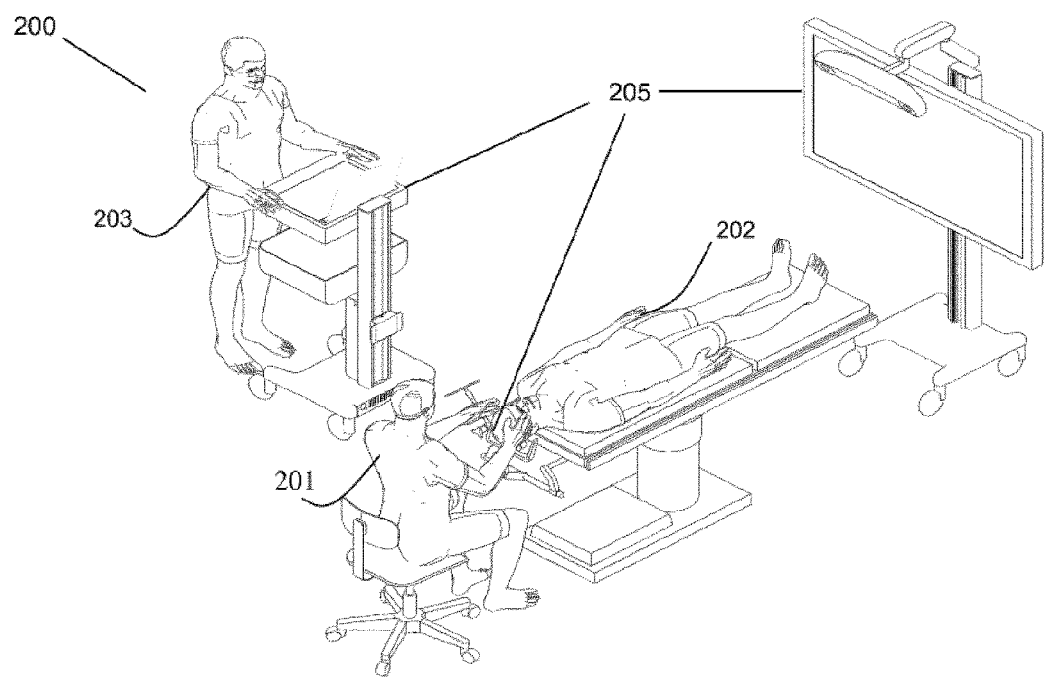
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
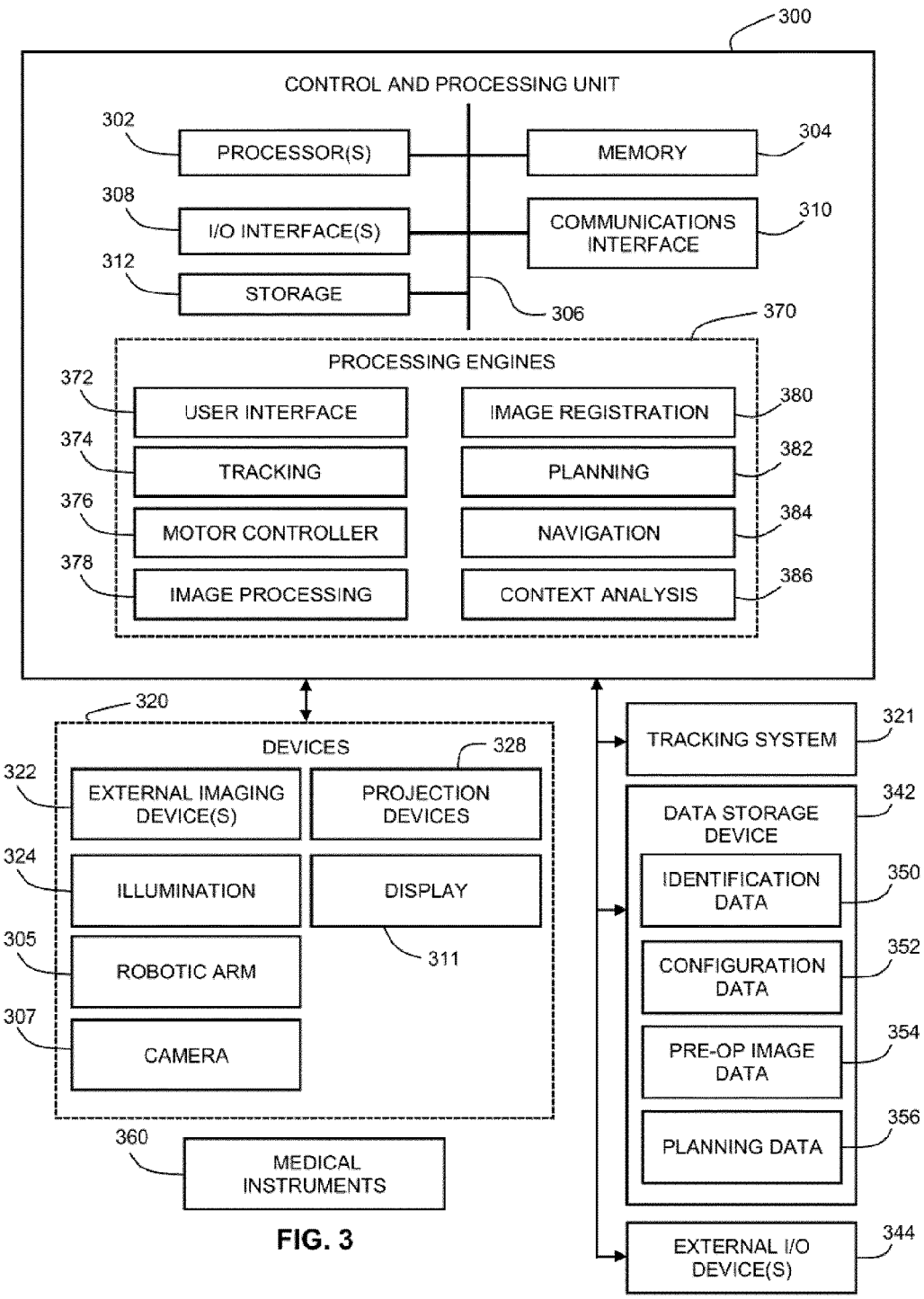
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 205 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a positioning device arm 305, one or more projection devices 328, and one or more displays 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
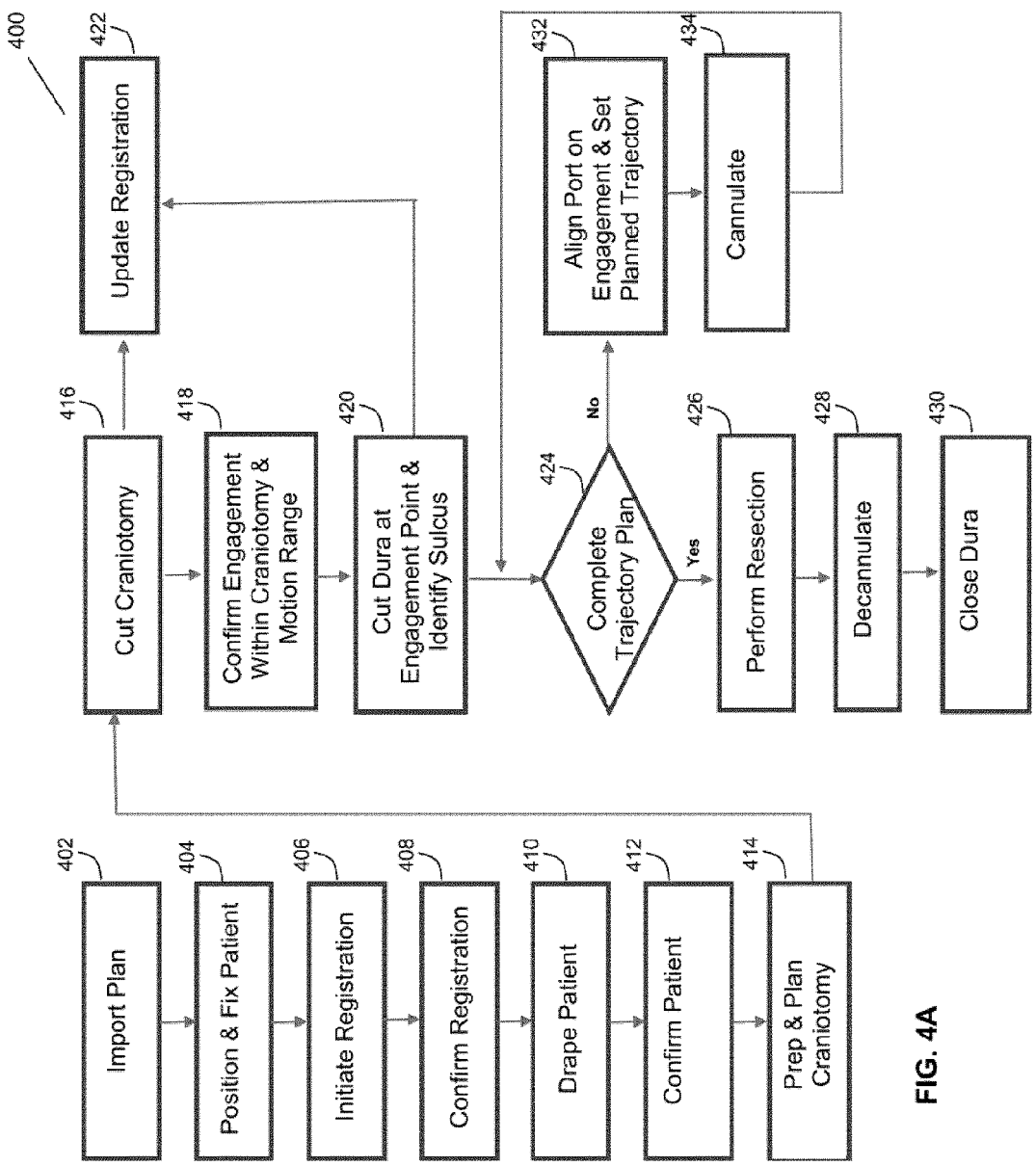
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are both hereby incorporated by reference in their entirety.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower 201.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
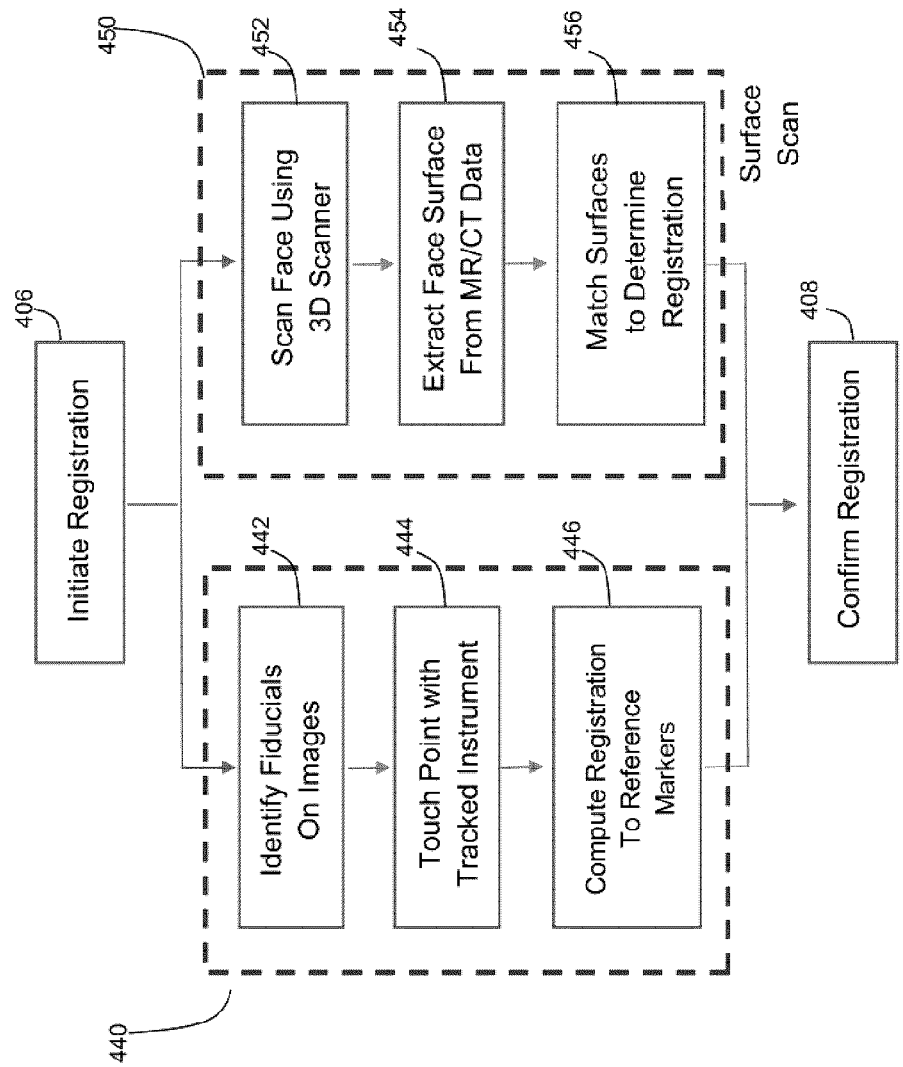
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
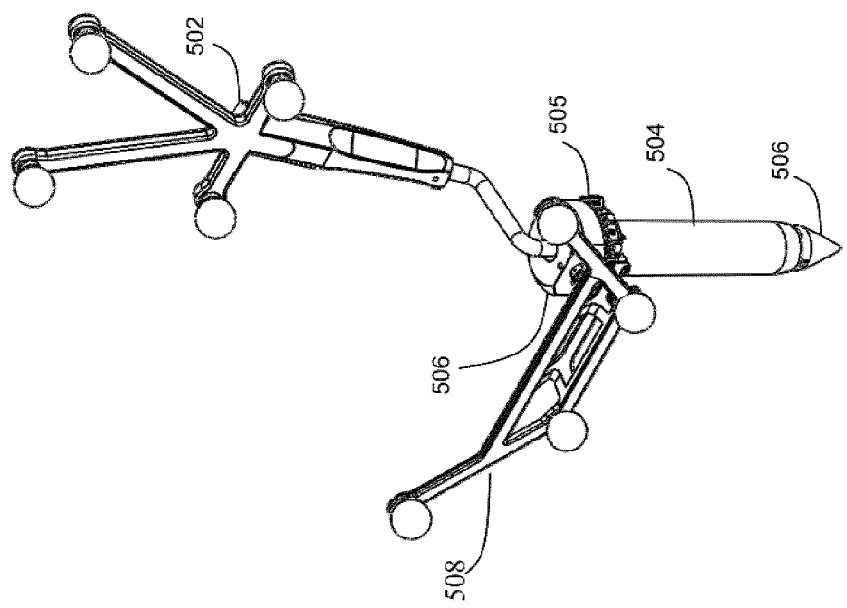
FIG. 5 is a perspective drawing illustrating an exemplary context for aspects of the present application showing conventional solutions to tracking an access port, port tracking tool, and medical tool.

Referring to FIG. 5, a perspective drawing is shown illustrating an exemplary context for aspects of the present application including a conventional medical tool 502, an access port 504, an obturator 506, and a conventional port tracking tool 508. Port-based neurosurgery is a minimally-invasive procedure. Currently, a navigation system such as the medical navigation system 205 using the control and processing unit 300 is used to track a pointer tool, such as the medical tool 502, inserted into the obturator 506 of the port sheath (e.g., the access port 504) during the approach phase of the surgery. Navigation in approach facilitates placement of the sheath or access port in the correct location close to the target area of the brain along a planned trajectory. When the navigation system 205 is used in conventional approaches, the pointer tool (e.g., the medical tool 502) is introduced into the sheath or port momentarily to orient the surgeon relative to preoperative Magnetic Resonance (MR) or Computed Tomography (CT) images.

There are at least two opportunities to solve problems by tracking the access port 504 continuously. First, in approach, the final step is to decant the sheath or access port 504 by moving the sheath or access port 504 down to the tip of the obturator 506. Often, surgeons who are new to the procedure will retract the obturator 506 instead of moving the access port 504 down. Since the access port 504 is not tracked, it is not clear from the medical navigation system display (e.g., the display 311) that the access port 504 ended up in the wrong location. Second, during resection, real-time tracking of the access port 504 would provide the surgeon with a continuous view of where he is operating (e.g., per preoperative images). The use of a tracked access port 504 would also reduce the need for the surgeon to put down his surgical tool(s) in order to reintroduce the navigated pointer tool 502 down the access port 504. Yet another possible benefit is that if the sheath or access port 504 is displaced along the length of the obturator 506 during approach, tracking the access port 504 continuously allows for detection and display of the displacement to the surgeon.

Conventional approaches to continuous tracking of medical tools place tracking markers such as reflective tracking spheres on the medical tool 502 and/or the port tracking tool 508 so that the medical tool 502 and/or the port tracking tool 508 may be tracked by a tracking camera. This system occupies considerable space and can sometimes be tedious to set up. If the reflective markers are blocked by any object, the IR camera cannot detect the tool position accurately. The presence of the multiple reflective tracking spheres on the tools can also obstruct the working space of the surgeon or medical professional.

One aspect of the present application adopts one or more gyroscopes and/or accelerometers to create a real time medical tool tracking system. The gyroscope and/or accelerometer may be attached to a positioning device arm, an access port, a pointer, or a patient. In one example, during navigation, the navigation system 205 may use tracking information to determine with a high degree of precision the distance between a camera and the access port 504 in order to perform an improved auto-focus. Compared with conventional navigation systems using reflective tracking markers, the IR camera, marker tree and reflective tracking markers (e.g., the port tracking tool 508) may be removed and replaced by an inertial system using gyroscopes and/or accelerometers.

Gyroscope technology has been rapidly developing, such as Micro-Electro-Mechanical Systems (MEMS) gyroscopes, laser gyroscopes, and Nano-gyroscopes. Nano-gyroscopes have been built by several labs and research groups and provide the opportunity to integrate very small and energy efficient sensors into new applications. An inertial system may generate 3D tracking information and tool trajectory information for display on a display screen for reference by a surgeon. In one example, this 3D information may be used to optimize the trajectory of a positioning device arm for surgery and save operating room setup time and simulate tool positions and dynamic parameters.

One aspect of the present application may aim to provide system modeling and position tracking methods, minimize the amount of gyroscopes and accelerometers needed in a particular application, optimize the sensor location on the access port 504, positioning device arm end effector, positioning device arm joint, or patient, providing surgical tool dynamic parameters and offer a distance measurement precision of 1 mm or less.

Additionally, the gyroscope and accelerometer may be used to obtain imaging deblurring. For example, when using a motorized scope setting at highest magnification, shaking of the access port may cause image blurring. The gyroscope and accelerometer may monitor the access port motion and generate a motion signal that is sent to the navigation system 205. In one example, the navigation system 205 may create a blur matrix and process images provided by a scope to reduce blurring. This may function in a similar way to the image stabilization functions of camera lenses. This may provide a benefit for motorized scope motion deblurring.

Figure 6:
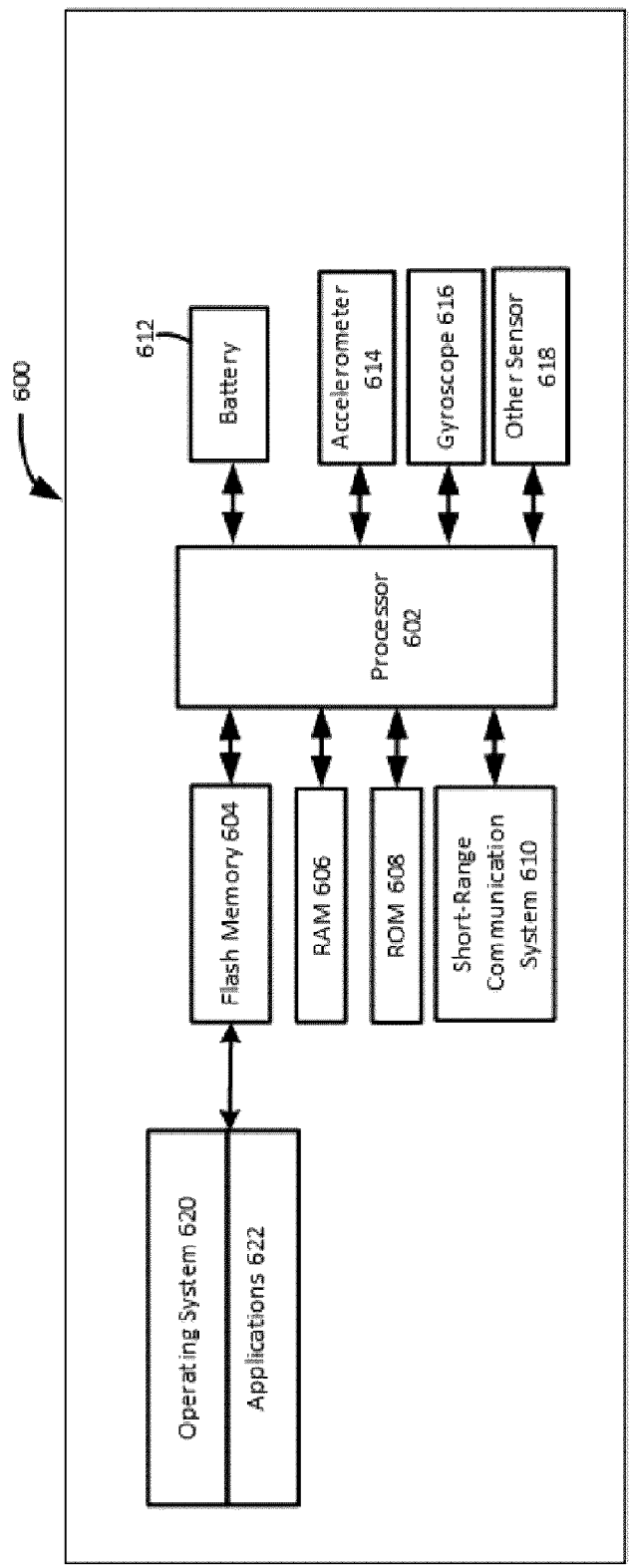
FIG. 6 is a block diagram showing an exemplary sensor module for use with a medical device and a navigation system.

Referring now to FIG. 6, a block diagram is shown illustrating an exemplary sensor module 600 for use with a medical device and a navigation system. The sensor module 600 may be used for attachment to a medical device and for use with a medical navigation system, such as the medical navigation system 205 including the control and processing unit or system 300. The sensor module 600 generally includes a housing for housing components of the sensor module (shown below in connection with FIGS. 7-9) and for attaching to the medical device. The sensor module 600 includes a processor 602 housed in the housing, a memory 604 coupled to the processor 602, a communication component coupled to the processor such as the short-range communication system 610, a battery 612 coupled to the processor, and a sensor coupled to the processor. In one example, the sensor may be an accelerometer 614, a gyroscope 616, or any other suitable sensor 618, such as a magnetometer. While the flash memory 604 is provided as one example of a memory coupled to the processor 602, other or additional forms of memory may be coupled to the processor 602, such as a RAM 606 and a ROM 608. The sensor module 600 may operate under stored program control, for example under the direction of an operating system or firmware 620 and/or one or more applications 622, which may be stored in the flash memory 604.

In one example, the sensor module 600 may include at least one of the accelerometer 614 and the gyroscope 616. Either one or both of the accelerometer 614 and the gyroscope 616 may be a three axis X-Y-Z sensor. In some cases, sensors providing less than three axes of data may be used. Examples for the gyroscope 616 include a MEMS gyroscope, a laser gyroscope, and a nano-gyroscope and examples for the accelerometer 614 include a laser accelerometer, a nano-accelerometer, and a MEMS accelerometer. Accelerometers and gyroscopes are well known and are not described in detail herein, however any suitable known or yet to be developed sensors may be used in or with the sensor module 600 to meet the design criteria of a particular application.

The communication component 610 includes a wireless communications component and, for example, may use existing wireless standards such as Bluetooth, Wifi, GSM, CDMA, LTE or Zigbee, or may use a suitable yet to be developed wireless standard for communication with a wireless communications subsystem (e.g., the communications interface 310) of the control and processing unit 300 of the medical navigation system 205.

In one example, the sensor module 600 may be attached to a positioning device arm, an access port, a pointer, a patient, or any other suitable medical device or tool. Some examples in this regard are presented below in connection with FIGS. 7-9.

Figure 7:
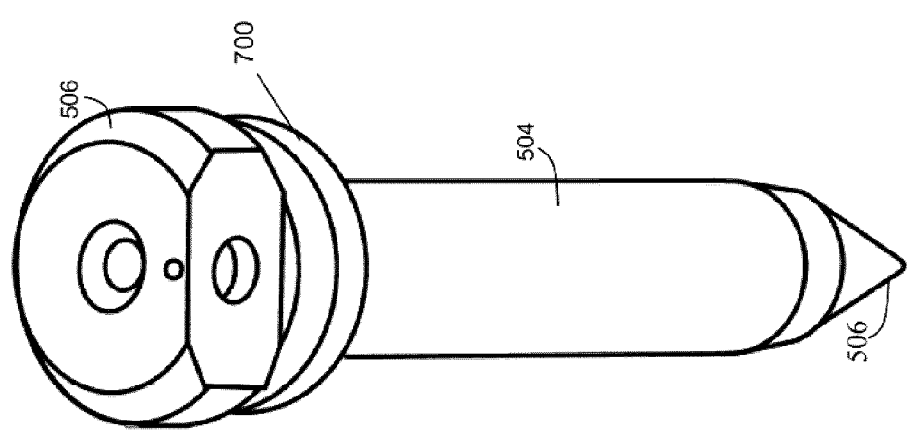
FIG. 7 is a perspective drawing illustrating an exemplary package for the sensor module shown in FIG. 6.

Referring to FIG. 7, a perspective drawing is shown illustrating an exemplary package or housing 700 for the sensor module 600 shown in FIG. 6. In the example shown in FIG. 7, the access port 504 is shown with the obturator 506 inserted into the access port 504. The package 700 for the sensor module 600 is formed as a collar that may be placed over the access port 504. In one example, the package or housing 700 may be disc shaped with a hole in the center and have an inside diameter that is substantially equal to the outside diameter of the access port 504 so that the disc shaped housing 700 may be securely fastened in position on the access port 504 so that the sensor module 600 does not move relative to the access port 504.

Figure 8:
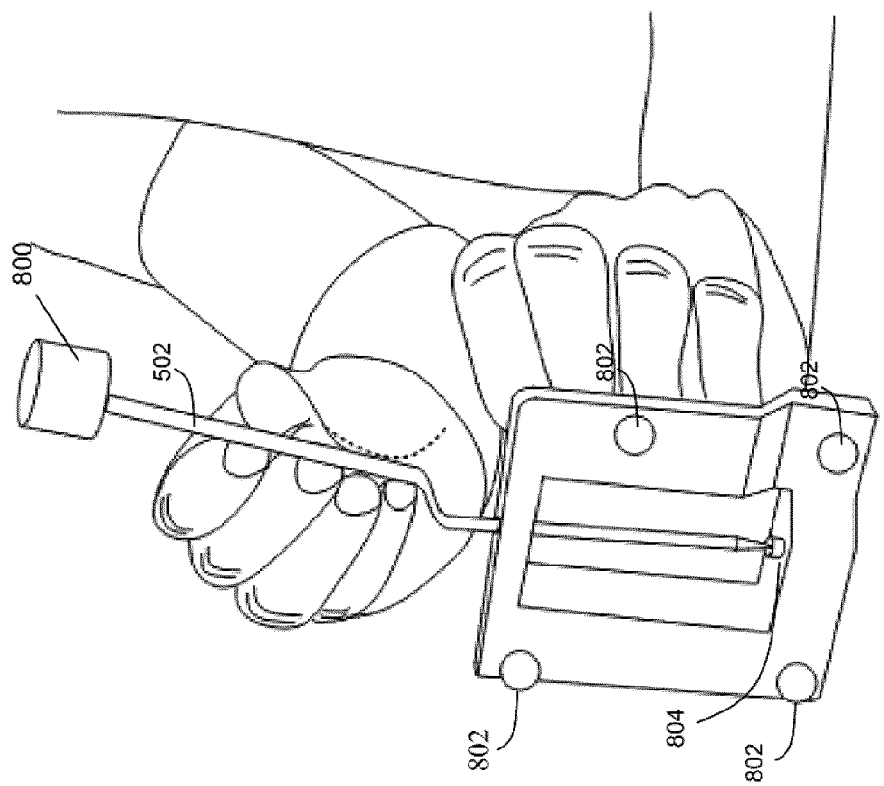
FIG. 8 is a perspective drawing illustrating another exemplary package for the sensor module shown in FIG. 6.

Referring to FIG. 8, a perspective drawing is shown illustrating another exemplary package or housing 800 for the sensor module 600 shown in FIG. 6. In FIG. 8, another example of the pointer tool 502 is shown. In FIG. 8, the pointer tool 502 is inserted into a calibration block having reflective tracking makers 802 that are visible by a camera of the medical navigation system 205. The calibration block has known dimensions where the position of a floor of a divot 804 is known relative to the tracking makers 802, so that a point of the pointer tool 502 that rests in the divot 504 has a known position in 3D space. The medical navigation system 205 can then learn the position of the sensor module 800 relative to the tip of the pointer tool 502, based on the system 205 having data relating to the position in space of the calibration block from the location of tracking markers 802 and based on a recorded geometry of the pointer tool 502. The sensor module 800 shown in FIG. 8 may be cylindrical in shape and have a recess on a bottom side of the sensor module 800 so that the sensor module 800 may be fitted to a top end of the pointer tool 502.

The package or housing 800 may be suitably modified to apply to other surgical tools, such as a scalpel or other cutting device. In one example, a surgical tool may be monitored using data provided by the gyroscope 616 and/or the accelerometer 614. Providing information concerning the dynamic status of the tool to the surgeon (e.g., on the display 311) may be helpful so that the surgeon can control his hand power and/or tool angle to cut or remove tissue, etc. Further, these surgical tools may be visualized as visual representations on the navigation system as tracked instruments.

Figure 9:
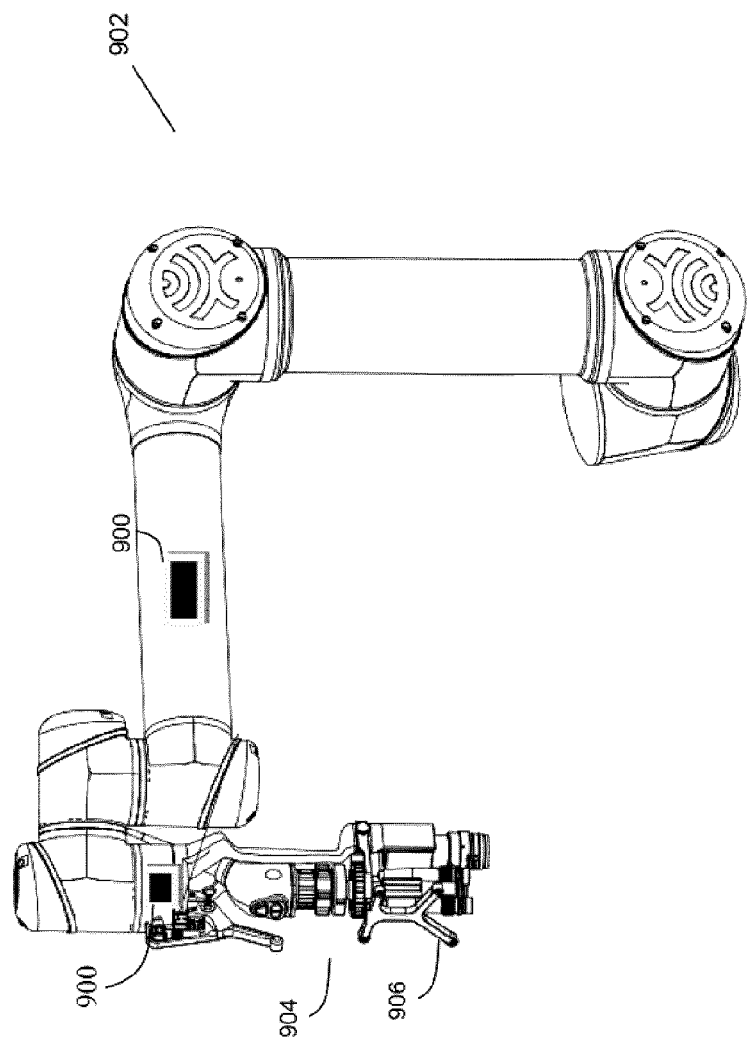
FIG. 9 is a perspective drawing illustrating another exemplary package for the sensor module shown in FIG. 6.

Referring to FIG. 9, a perspective drawing is shown illustrating another exemplary package or housing 900 for the sensor module 600 shown in FIG. 6. FIG. 9 shows a positioning device 902 that has a number of arms and joints, including an end effector 904. The package or housing 900 may be square, rectangular, round or any other suitable shape and may have a relatively thin profile. In one example, the package or housing 900 may take the form of a sticker or a band that is easily affixed to an arm of the position device 900 or a mating component that connects to the end effector 904. In one example, the package or housing 900 may attach directly to the end effector 904. In some examples, the package or housing 900 may allow for a tracking frame 906 that includes tracking markers affixed thereto to be removed from the end effector 904, therefore making the end effector 904 less cluttered and easier to interface with.

In one example, a housing for the sensor module 600 may be formed as a removable collar that slips onto and/or wraps around an access port, a medical tool, a videoscope, an automated positioning arm, or any other suitable medical device. The housing for the sensor module 600 may be elastic such that the housing can be stretched and positioned on an access port, a medical tool, a videoscope, an automated positioning arm, or any other suitable medical device, at which point the housing then retracts to its original size forming a snug fit to the device on which the sensor module 600 was positioned. In another example, the housing for the sensor module 600 may be substantially inelastic and may include a fastening device such as a latch and hook or Velcro to affix the sensor module 600 into position on an access port, a medical tool, a videoscope, an automated positioning arm, or any other suitable medical device. While three examples of packages 700, 800, 900 for the sensor module 600 are shown in FIGS. 7, 8 and 9 and additional examples are described above for affixing the sensor module 600 to a medical tool or device, any suitable package and securing method or mechanism may be used to meet the design criteria of a particular application.

Figure 10:
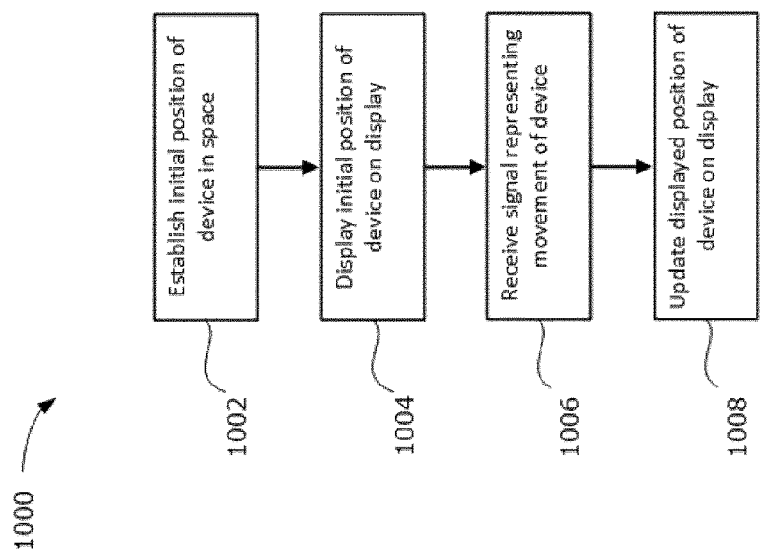
FIG. 10 is a flow chart illustrating a method for tracking a location of a medical device using the sensor module of FIG. 6.

Referring now to FIG. 10, a flow chart illustrating a method 1000 for tracking a location of a medical device using the sensor module 600 of FIG. 6 is shown. The method 1000 may establish and monitor a position of a medical device and the method 1000 may be executed by a computing device of a medical navigation system (e.g., the control and processing unit 300 of medical navigation system 205, including the processor 302 coupled to the memory 304 and the wireless communication component 310 and the display 311 for displaying an image).

At a first block 1002, the initial position in space of the medical device is established. For the purpose of example with respect to the method 1000, the medical device may be the access port 504 shown in FIG. 5. Gyroscopes and accelerometers provide data related to changes in space and these sensors do not typically provide data that allows for the determination of an absolute starting position in space. Therefore, a position in space of the medical device is first established, for example by temporarily affixing the tracking tool 508 to the access port 504. A camera, such as the camera 307, may then detect the presence of the tracking markers affixed to the tracking tool 504 and the medical navigation system 205 may then compute the position in space of the access port 504 relative to other markers, which might be affixed to the patient and/or the bed on which the patient is positioned, a positioning device such as a robotic arm, or any other medical tool or piece of equipment for which positioning data relative to the access port 504 is needed to complete the medical procedure. In other words, a location in space of tracking markers affixed to the tracking tool 508 temporarily placed on the medical device is detected using an image signal provided to the processor 302 by the camera, such as the camera 307.

Next, at a block 1004, the initial position of the medical device may be displayed on the display (e.g., the display 311) when the initial position is established by the medical navigation system 205. The position shown on the display may be relative to other markers, which might be affixed to the patient and/or the bed on which the patient is positioned, a positioning device such as a robotic arm, or any other medical tool or piece of equipment for which positioning data relative to the access port 504 is needed to complete the medical procedure. Images such as X-RAY images, CT-Scan Images, or MRI images may be overlaid on the display 311 so that the position of the medical device is shown relative to the patient and the surgical site of interest.

Next, at a block 1006, the medical navigation system 205 may begin receiving via the wireless communication component (e.g., via communications interface 310) a signal representing movement of the medical device. The signal may be generated by the accelerometer 614, the gyroscope 616, and/or other sensors 618, processed by processor 602, and transmitted by short range communications system 610. In another example, the signal may include information provided by the accelerometer 614 and the gyroscope 616 housed in the sensor module 600 housing 700 and attached to the medical device, such as the access port 504. The medical navigation system 205 may use the received signal to determine movement of the medical device subsequent to its initial position. Aids used to determine the initial position of the medical device, such as the tracking tool 508, may be removed from the medical device once the initial position is determined. The signal that represents movement of the medical device may include data representing pose, pitch, orientation, rotation, and/or xyz position (e.g., position of the device in either a cartesian or polar coordinate based system) of the medical device. Any other suitable measurements or data concerning the movement of the medical device may also be used.

Next, at a block 1008, the position of the medical device on the display 311 is updated when the received signal represents movement of the medical device. In one example, any updating of the position of the medical device on the display 311 may be subject to a threshold such that insignificant movements are not reflected on the display 311.

In one example, initial position determination made by the medical navigation system 205 (e.g., block 1002) may be transmitted to the sensor module 600 and the sensor module 600 may record and subsequently internally update its known position in space (e.g., saved in the memory 604). In some examples, the sensor module 600 may be used in conjunction with an optical tracking system to function as a positioning backup system to aid a positioning device to perform a periodic refresh, return to a default position, recalibrate a position, return to a particular pose, or even provide a bump sensor for the positioning device to alert the medical navigation system 205 when a positioning device may have been bumped out of position. Data from the sensor module 600 may also be used to move the tracking camera to recapture line of sight with optical tracking markers when the line of sight between the tracking makers and the tracking camera has been obstructed.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A medical navigation system, comprising:
   a computing device having a processor coupled to a memory, a wireless communication component and a display for displaying an image;
   a sensor module attached to a medical device, the sensor module including:
     a housing for housing components of the sensor module and for attaching to the medical device, the housing including a fastening device to removably attach the sensor module to a surface of the medical device;
     a processor housed in the housing;
     a memory coupled to the processor;
     a wireless communication component coupled to the processor;
     a battery coupled to the processor;
     a sensor coupled to the processor, the sensor including at least one of an accelerometer and a gyroscope;
     wherein the sensor is configured to generate a signal representing movement of the medical device, the wireless communication component of the sensor module being configured to transmit the signal wirelessly;
   a first set of tracking markers configured to be temporarily coupled to the medical device; and
   a camera coupled to the computing device for detecting a location of the first set of tracking markers, the sensor module being free of any markers detectable by the camera;
   wherein the computing device is configured to:
     receive the signal from the sensor module via the wireless communication component of the computing device;
     determine the initial position of the medical device based on the location of the first set of tracking markers detected by the camera and not based on the signal from the sensor module;
     display an initial position of the medical device on the display;
     when a line of sight from the camera to the first set of tracking markers is not available, update the display to reflect movement of the medical device subsequent to the initial position, using only the signal from the sensor module and not based on detection of any tracking markers by the camera; and
     when the line of sight from the camera to the first set of tracking markers becomes available, further update the display, to reflect further movement of the medical device when the first set of tracking markers are detectable by the camera, based on detection of the first set of tracking markers by the camera and not based on the signal from the sensor module.

2. The medical navigation system according to claim 1, wherein the fastening device is selected from the group consisting of a latch, a hook, Velcro, and a sticker and the movement further comprises real-time tracking of the medical device.

3. The medical navigation system according to claim 1, wherein the gyroscope is selected from the group consisting of a MEMS gyroscope, a laser gyroscope, and a nano-gyroscope and the accelerometer is selected from the group consisting of a laser accelerometer, a nano-accelerometer, and a MEMS accelerometer.

4. The medical navigation system according to claim 1, wherein the sensor module includes a three axis X-Y-Z sensor.

5. The medical navigation system according to claim 1, wherein the computing device wireless communication component and the sensor module wireless communication component both use a protocol selected from the group consisting of Bluetooth, Wifi, iRDA (Infrared) and Zigbee.

6. The medical navigation system according to claim 1, wherein the medical device is selected from the group consisting of a positioning device arm, an access port, and a pointer.

7. The medical navigation system according to claim 1, wherein there is a plurality of medical devices and a plurality of sensor modules attached to the plurality of medical devices.

8. The medical navigation system according to claim 7, wherein one of the medical devices is a positioning device arm, and there is a plurality of sensor modules attached to the positioning device arm.

9. The medical navigation system according to claim 1, further comprising:

a calibration block configured to be temporarily coupled at a known relationship to the medical device, a second set of tracking markers being mounted on the calibration block at known positions, the camera being configured for detecting a location of the second set of tracking markers;

wherein the computing device is further configured to calculate position of the sensor module relative to a tip of the medical device, based on the known positions of the second set of tracking markers relative to the calibration block, the location of the second set of tracking markers detected by the camera, the known geometry of the medical device, and the known relationship between the calibration block and the medical device when coupled thereto.

10. A method of establishing and monitoring a position of a medical device, the method for use on a computing device of a medical navigation system, the computing device having a processor coupled to a memory, a wireless communication component, a display for displaying an image and a camera for detecting location of tracking markers, the method comprising:

establishing an initial position of the medical device in space by:

receiving from the camera a signal representing a location in space of a first set of tracking markers temporarily placed on the medical device; and determining the initial position of the medical device based on the location of the first set of tracking markers detected by the camera;

displaying on the display the initial position of the medical device;

receiving via the wireless communication component a signal representing movement of the medical device, the signal including information provided by an accelerometer and a gyroscope housed in a housing of a sensor module attached to the medical device, the housing including a fastening device to removably attach the sensor module to a surface of the medical device, the sensor module being free of any markers detectable by the camera; and when a line of sight from the camera to the first set of tracking markers is not available, updating the display to reflect movement of the medical device, subsequent to the initial position, based on only the signal representing movement of the medical device received from the sensor module and not based on detection of any tracking markers by the camera; and when the line of sight from the camera to the first set of tracking markers becomes available, further updating the display, to reflect further movement of the medical device when the first set of tracking markers are detectable by the camera, based on detection of the first set of tracking markers by the camera and not based on the signal from the sensor module.

11. The method according to claim 10, further comprising:

receiving from the camera a signal representing a location in space of a second set of tracking markers mounted on a calibration block at known positions, the calibration block being temporarily coupled to the medical device at a known relationship; and calculating position of the sensor module relative to a tip of the medical device, based on the known positions of the second set of tracking markers relative to the calibration block the location of the second set of tracking markers detected by the camera, the known geometry of the medical device, and the known relationship between the calibration block and the medical device when coupled thereto.

12. The method according to claim 10, wherein there is a plurality of medical devices and a plurality of sensor modules attached to the plurality of medical devices.

13. The method according to claim 12, wherein one of the medical devices is a positioning device arm, and there is a plurality of sensor modules attached to the positioning device arm.

* * * * *